United States Patent [19]

Schmidt et al.

[11] 4,267,397
[45] May 12, 1981

[54] HYDRATION OF OLEFINIC COMPOUNDS WITH DILUTE SULFURIC ACID AND COBALT SULFATE

[75] Inventors: Robert J. Schmidt, Hoffman Estates; Tamotsu Imai, Mt. Prospect, both of Ill.

[73] Assignee: UOP Inc., Des Plaines, Ill.

[21] Appl. No.: 106,312

[22] Filed: Dec. 21, 1979

[51] Int. Cl.³ .............................................. C07C 29/04
[52] U.S. Cl. .................................. 568/899; 568/695; 568/696
[58] Field of Search .......................................... 568/899

[56] References Cited

U.S. PATENT DOCUMENTS

| 1,438,123 | 12/1922 | McElroy | 568/899 |
| 2,045,842 | 6/1936 | Dreyfus | 568/899 |
| 2,070,258 | 2/1937 | Coleman et al. | 568/899 |
| 2,112,793 | 3/1938 | Stanley et al. | 568/899 |
| 2,228,027 | 1/1941 | Bent | 568/899 |
| 3,352,930 | 11/1967 | Mention | 568/899 |

FOREIGN PATENT DOCUMENTS 44-9203 4/1969 Japan ........................................ 568/899

Primary Examiner—Joseph E. Evans
Attorney, Agent, or Firm—James R. Hoatson, Jr.; Raymond H. Nelson; William H. Page, II

[57] ABSTRACT

Olefinic compounds, and particularly olefinic hydrocarbons, containing from 2 to about 4 carbon atoms may be subjected to a direct hydration process utilizing a dilute aqueous sulfuric acid to treat the olefin at reaction conditions which will include a temperature in the range of from about 100° to about 300° C. and a pressure in the range of from about 1 to about 250 atmospheres. In addition, if so desired, a transition metal sulfate may also be present in the reaction mixture.

4 Claims, 1 Drawing Figure

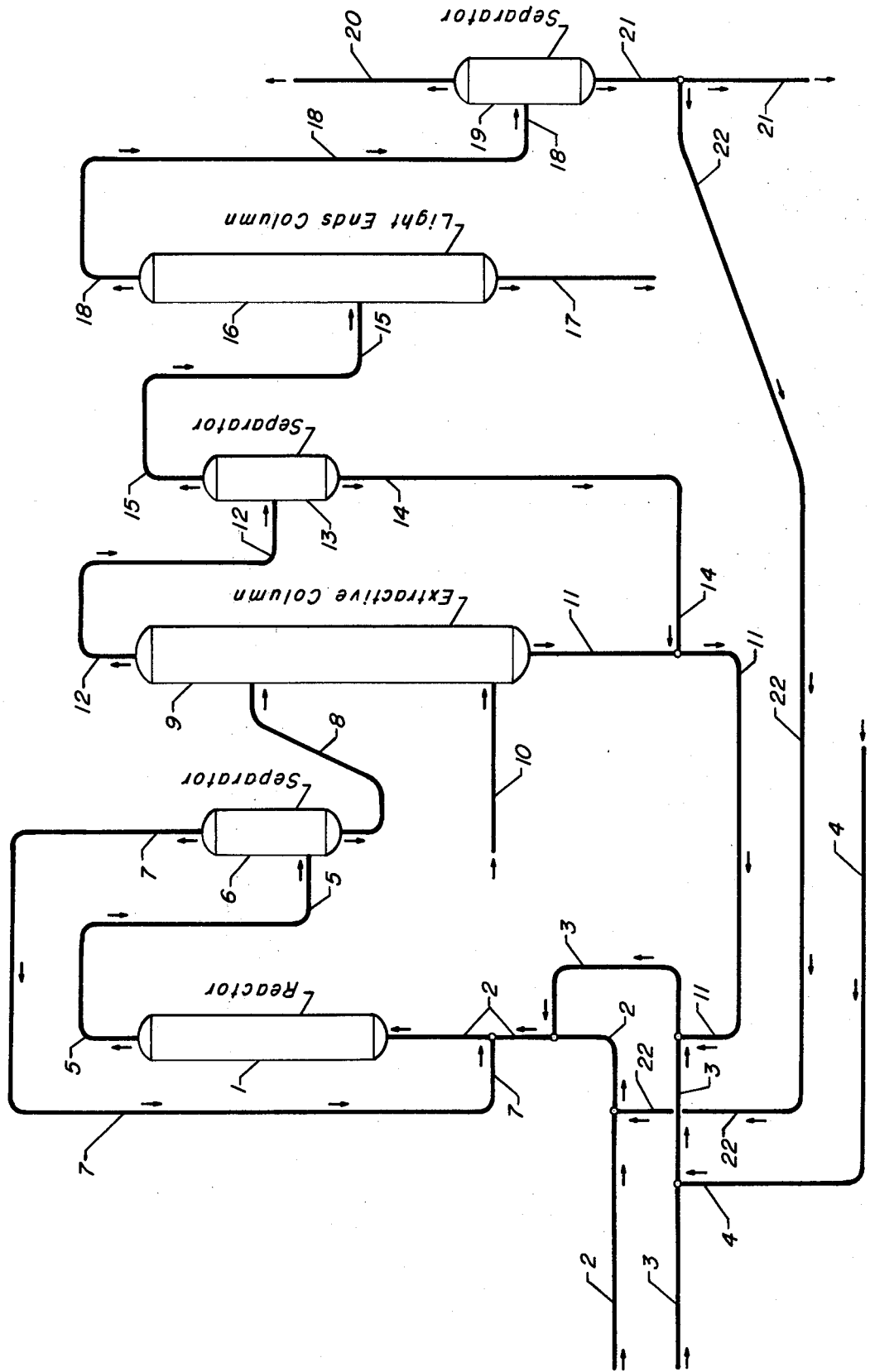

HYDRATION OF OLEFINIC COMPOUNDS WITH DILUTE SULFURIC ACID AND COBALT SULFATE

BACKGROUND OF THE INVENTION

Heretofore olefinic compounds containing from 2 to about 4 carbon atoms were utilized as starting materials for the production of alcohols. The alcohols were conventionally produced by the hydration of the olefins using a relatively concentrated sulfuric acid solution, that is, a solution which contained more than about 55% sulfuric acid. The olefin was converted to the sulfuric acid ester in one stage and was thereafter hydrolyzed to the corresponding alcohol after lowering the acid content of the solution to less than 40%. The utilization of a relatively concentrated sulfuric acid solution to effect the hydration of the olefins possessed inherent disadvantages. For example, it is costly to concentrate the dilute sulfuric acid solution. In addition, it is well known that concentrated sulfuric acid is a dangerous chemical and therefore precautions must be taken when utilizing this chemical in order to avoid accidents which may occur. Furthermore, corrosion problems may also arise and thus would necessitate the use of relatively expensive equipment in order to efficiently produce the desired alcohol.

As will hereinafter be shown in greater detail, it has now been discovered that in contrast to the conventional process, it is possible to effect a direct hydration of the olefinic compounds in one step to produce the corresponding alcohol. This result is obtained by utilizing a dilute sulfuric acid solution of the type hereinafter set forth in greater detail and, in addition, by utilizing a transition metal sulfate it is possible to reduce any corrosion problems which may be present in the process.

This invention relates to a process for the direct hydration of olefinic compounds. More specifically, the invention is concerned with a one step direct hydration process of olefinic compounds to the corresponding alcohols by utilizing a sulfuric acid solution which is relatively direct in nature.

Alcohols constitute an important class of chemicals which find a wide variety of uses in industry. For example, one of the most common alcohols, namely, ethyl alcohol, may be used as a solvent and extraction medium, as a component in the manufacture of intermediates organic derivatives, dyes, synthetic drugs, synthetic rubber, detergents, cleaning solutions, surface coatings, cosmetics, pharmaceuticals, beverages, automobile radiator antifreeze, etc. Likewise, isopropyl alcohol is used in the manufacture of acetone, diacetone alcohol as a solvent for essential and other oils, alkaloids, gums, resins, etc., as a latent solvent for cellulose derivatives, as an antistalling agent or deicing agent for liquid fuels, in pharmaceuticals, perfumes, liquors, preservatives, rocket fuels, etc. The butyl alcohols such as n-butyl alcohol is used in the preparation of esters, as a solvent for resins and coatings, in plasticizers, hydraulic fluids, etc.; while sec-butyl alcohol may be used in the preparation of methyl ethyl ketone, and as a solvent in varnishes, lacquers, and paint removers.

It is therefore an object of this invention to provide a process for the hydration of olefins.

A further object of this invention is to provide a one step direct hydration process of olefins to the corresponding alcohols utilizing a dilute sulfuric acid solution.

In one aspect an embodiment of this invention resides in a process for the direct hydration of an olefinic compound which comprises treating said olefin with a dilute sulfuric acid solution at reaction conditions and recovering the resultant hydrated compound.

A specific embodiment of this invention is found in a process for the direct hydration of an olefinic compound which comprises treating propylene with a dilute sulfuric acid solution in which the concentration of sulfuric acid in said solution is in a range of from about 0.05 to about 40% by weight and in the presence of copper sulfate at a temperature in the range of from about 100° to about 300° C. and a pressure in the range of from about 1 to about 250 atmospheres, and recovering the resultant isopropyl alcohol.

Other objects and embodiments will be found in the following further detailed description of the present invention.

As hereinbefore set forth the present invention is concerned with a process for the direct hydration of olefinic compounds, and particularly olefinic hydrocarbons containing from 2 to about 4 carbon atoms in a one step process. Examples of olefins which may be subjected to the direct hydration process of the present invention will include ethylene, propylene, n-butylene and isobutylene. The hydration of the olefins is effected by treating said olefin in the presence of a dilute aqueous sulfuric acid solution in which the concentration of sulfuric acid present therein is in a range of from about 0.05 to about 40% by weight. The reaction conditions under which the hydration is effected will include elevated temperatures in the range of from about 100° to about 300° C. and elevated or superatmospheric pressures in the range of from about 1 to about 250 atmospheres. The superatmospheric pressure may be afforded by the autogenous pressure of the olefin which is undergoing hydration or, if so desired, the olefin may provide only a partial pressure, the remainder of the desired operating pressure being supplied by the introduction of a substantially inert gas such as nitrogen, helium, argon, etc., into the reaction vessel. In addition to the operating parameters hereinbefore discussed, the mole ratio of water to olefin constitutes another operating variable, the mole ratio of water to olefin being in a range of from about 1:1 to about 40:1 moles of water per mole of olefin.

While the hydration reaction is effected in the presence of a dilute aqueous sulfuric acid solution, it is also contemplated within the scope of this invention that transition metal sulfates may also be present in the reaction mixture. The presence of these transition metal sulfates will greatly reduce the sulfuric acid concentration level and concomitantly also reduce the corrosion problems which may be present in the reaction system. Examples of transition metal sulfates which may be employed will include copper sulfate, nickel sulfate, zinc sulfate, cadmium sulfate, cobalt sulfate, chromium sulfate, molybdenum sulfate, titanium sulfate, zirconium sulfate, vanadium sulfate, etc. It is to be understood that these metal sulfates are only representative of the class of transition metal sulfates which may be employed, and that the present invention is not necessarily limited thereto. In another embodiment of the invention it is contemplated that an aqueous solution of a transition metal sulfate of the type hereinbefore set forth may be employed as the catalyst for the hydration reaction. However, use of the transition metal sulfate per se without the presence of a dilute sulfuric acid may not necessarily result in equivalent results as pertaining to the obtention of the desired hydrated compound.

The process of this invention may be effected in any suitable manner and may comprise either a batch or continuous type operation. For example, when a batch type operation is used a quantity of the dilute aqueous sulfuric acid solution is placed in an appropriate apparatus such as an autoclave of the rotating, mixing or stirring type. In addition, an added amount of water may also be placed in the autoclave to bring the desired molar ratio of water to hydrocarbon within the desired range. The autoclave is then sealed and the olefinic hydrocarbon which is to be hydrated is charged thereto along with any inert gas, if so desired, until the desired initial operating pressure has been reached. The autoclave is then heated to the predetermined operating temperature and maintained thereat for a period of time which may range from about 0.05 up to about 10 hours or more in duration. Upon completion of the reaction time the autoclave and contents thereof are allowed to return to room temperature, the excess pressure is discharged and the autoclave is opened. The reaction mixture is recovered therefrom and subjected to conventional means of separation which may include extraction, fractional distillation, etc., whereby the desired alcohol is separated from any unreacted starting material and/or side products which may have formed during the reaction and recovered.

It is also contemplated within the scope of this invention that the hydration reaction may be effected in a continuous manner. When such an operation is to be used the olefin and water along with any dilute aqueous sulfuric acid solution is charged to a reactor which is maintained at the proper operating conditions of temperature and pressure. After remaining in the reactor for a predetermined period of time, the effluent is continuously withdrawn and passed to a separation stage wherein the products are separated from any unreacted olefin, said unreacted olefin being recycled to the reaction zone to form a portion of the feed material. The bottoms from the separator which comprise the desired alcohol along with any side reaction products such as oligomers or ethers are then subjected to a distillation in an extraction column, said extraction being effected in the presence of an azeotropic solvent such as benzene, paraffins, olefins, etc., whereby the desired product may be separated from the aforesaid side reaction products and recovered.

BRIEF DESCRIPTION OF THE DRAWING

The present invention will be further illustrated with reference to the accompanying drawing which sets forth an illustrative flow diagram of one embodiment of the process of this invention. It is to be understood that various valves, pumps, etc., have been eliminated as not being essential to the complete understanding of the invention. However, the utilization of these as well as other similar appurtenances will become obvious as the drawing is described.

Referring now to the drawing, a charge stock comprising an olefinic hydrocarbon which may contain from 2 to about 4 carbon atoms or more is charged to reactor 1 through line 2. In addition, water is charged to reactor 1 through lines 2 and 3 and any start-up or make-up catalyst comprising sulfuric acid and, if so desired, a metal sulfate of the type hereinbefore set forth is also charged to reactor 1 through lines 2, 3 and 4. In hydration reactor 1 the charge stock is subjected to a hydration reaction at conditions of temperature and pressure within the range also hereinbefore set forth in greater detail. After hydration of the olefinic hydrocarbon to form the corresponding alcohol the reactor effluent is withdrawn from reactor 1 through line 5 and passed to separator 6. In separator 6 unreacted olefin is withdrawn overhead through line 7 and recycled to reactor 1 to form a portion of the feed material. The hydrated product is withdrawn from separator 6 through line 8 and passed to extractive distillation column 9. In extractive distillation column 9 the product is contacted with an azeotropic solvent such as benzene, cyclohexane, the isomeric pentanes, etc., which is charged to extractive distillation column 9 through line 10. In extractive distillation column 9 the catalyst comprising a dilute sulfuric acid solution and, if so desired, a metal sulfate is withdrawn from column 9 through line 11 and recycled back to hydration reactor 1 through lines 11 and 3. The product mixture which includes the solvent, the alcohol and any side reaction products which may have been formed such as ethers, oligomers, light ends, and water, are withdrawn from column 9 through line 12 and passed to a liquid/liquid separator 13. Water and any catalyst which may still have been present and which may have passed over with the products through line 12 is withdrawn from separator 13 through line 14 and admixed with other recycle catalyst in line 11 for further use in hydration reactor 1. The product stream which has been separated from any catalyst is withdrawn from separator 13 through line 15 and passed to light ends column 16. In column 16, the desired product comprising the alcohol and solvent is withdrawn through line 17 and passed to further azeotropic and purification columns, not shown in the drawing, whereby the solvent is stripped from the alcohol and the latter is recovered. The light ends from column 16 which may include ethers formed as side products during the reaction are withdrawn from column 16 through line 18 and passed to separator 19. In separator 19 the light ends are withdrawn through line 20 for further use as fuels while the ethers which may have been formed during the reaction is withdrawn through line 21. A portion of the ethers may be recovered and utilized as a fuel additive to enhance octane ratings of fuel such as gasoline while another portion may be recycled through line 22 to admix with the olefinic feed stock prior to entry into hydration reactor 1. The recycle of the ether to the olefinic feed stock is advantageous due to the obtention of improved yields of alcohol. The improved yield of the alcohol is due to an increased phase transfer or solubility of the olefin in the liquid phase.

As hereinbefore set forth, by utilizing a metal sulfate in the reaction mixture the corrosion problems which are inherent in the process may be minimized. It is to be understood, of course, that variations and modifications may be made to the illustrative flow scheme without necessarily departing from the scope of this invention.

The following examples are given for purposes of illustrating the process of this invention. However, it is to be understood that these examples are merely illustrative in nature, and that the present process is not necessarily limited thereto.

EXAMPLE I

To illustrate the process of this invention 404 grams of a 1% by weight aqueous sulfuric acid solution was placed in a rotating autoclave. The autoclave was then sealed and 31 grams of propylene were charged to the autoclave until an initial operating pressure of 65 atmospheres was reached. The mole ratio of water to propylene was 30:1 and the mole ratio of propylene to acid was 9.0:1. The autoclave was then heated to a temperature of 201° C. and maintained thereat for a period of 2 hours. At the end of this time, heating was discontinued, the autoclave was allowed to return to room temperature and the excess pressure was vented. The autoclave was then opened and the reaction mixture recovered therefrom. Analysis of the mixture by means of gas chromatography disclosed that there had been a 48% conversion of propylene with a 100% selectivity to isopropyl alcohol.

EXAMPLE II

The above experiment was repeated using 400 grams of a 2% by weight aqueous sulfuric acid solution and 31 grams of propylene, the difference between this example and Example I being that the mole ratio of the propylene to sulfuric acid was 4.5:1 moles of propylene per mole of acid instead of the 9:1 mole ratio of Example I. After pressuring the autoclave to 63.5 atmospheres and maintaining the autoclave at a temperature of 200° C. for a period of 2 hours, the reaction mixture was recovered in a manner similar to that set forth in the above example. Analysis of the reaction mixture by means of gas chromatography disclosed that there had been a 75% conversion of the propylene with a 99.4% selectivity to isopropyl alcohol, there also being observed a trace of diisopropyl ether.

EXAMPLE III

A series of further experiments were run in which the concentration of acid as well as the mole ratio of water to propylene, propylene to acid, temperature and pressure were varied. The results of these experiments are set forth in Table I.

TABLE I

| Run | Wt. % $H_2SO_4$ ($H_2O$ Solution) | Conditions T°C. | P(Atm) | Mole Ratio $C_3^=$/Acid | $H_2O/C_3^=$ | Conv. % | Alcohol Selectivity (Mole %) |
|---|---|---|---|---|---|---|---|
| A | 0.5 | 201 | 39.7 | 18 | 30 | 31 | 100 |
| B | 5 | 200 | 55.3 | 1.7 | 30 | 40 | 100 |
| C | 0.75 | 201 | 32.2 | 9.0 | 40 | 39 | 100 |
| D | 3 | 198 | 146 | 9.0 | 10 | 49 | 99.2 |
| E | 1 | 180 | 58.5 | 9.0 | 30 | 41 | 100 |
| F | 1 | 160 | 59.3 | 9.0 | 30 | 24 | 100 |
| G | 5 | 197 | 26.6 | 1.7 | 30 | 39 | 98.8 |
| H | 5 | 199 | 50.9 | 1.7 | 30 | 80 | 99.2 |
| I | 2 | 200 | 55.8 | 4.5 | 30 | 35 | 99.8 |
| J | 2 | 199 | 48.1 | 4.5 | 30 | 75 | 99.3 |

It is apparent from the above table that by utilizing a dilute sulfuric acid solution, it is possible to obtain a one step hydration of olefinic hydrocarbons, the selectivity being approximately 100% with only traces of diisopropyl ether being present in some of the examples.

EXAMPLE IV

To illustrate the proposition that some transition metal sulfates may be used to catalyze the direct hydration of olefins to alcohols, 12.3 grams of aluminum sulfate hexahydrate and 400 grams of water were placed in an 850 ml rotating autoclave. The autoclave was sealed and 31.6 grams of propylene were charged thereto until an initial operating pressure of 50 atmospheres was reached. The mole ratio of water to propylene was 30:1 and the mole ratio of propylene to sulfate was 9:1. The autoclave was then heated to a temperature of 200° C. and maintained thereat for a period of 1 hour. At the end of this time heating was discontinued and the autoclave was allowed to return to room temperature. The excess pressure was discharged, the autoclave was opened and the reaction mixture was recovered therefrom. Analysis of this mixture by means of gas chromatography disclosed that there had been a 24% conversion of the propylene with a selectivity to isopropyl alcohol of approximately 100%.

In a similar manner, propylene was treated in the presence of 13.2 grams of chromium sulfate pentahydrate at a temperature of 199° C. and an initial operating pressure of 51 atmospheres with identical mole ratios of water to propylene and propylene to sulfate for a period of 1 hour. Analysis of the reaction mixture disclosed that there had been a 15% conversion of the propylene with an approximate 100% selectivity to isopropyl alcohol. When the reaction mixture was recycled for a period of 1 hour at 200° C., it was found that there had been an approximate 45% conversion of the remaining propylene with a selectivity which was again approximately 100% isopropyl alcohol. A second recycle of this material resulted in an approximate 21% conversion of the remaining propylene with a selectivity of about 100% isopropyl alcohol.

When the above experiment was repeated using 13.1 grams of copper sulfate as the catalyst for the hydration reaction under similar conditions of temperature and pressure for a period of 2 hours, gas chromatography disclosed that there had been a 14% conversion of the propylene with about 100% selectivity to isopropyl alcohol.

EXAMPLE V

In this example 402 grams of a 1.0% sulfuric acid solution and 6.56 grams of copper sulfate were placed in a rotating autoclave having a capacity of 850 ml. The autoclave was sealed and propylene was passed in until an initial operating pressure of 64 atmospheres was reached. The autoclave was heated to a temperature of 198° C. and maintained thereat for a period of 2 hours. At the end of this period heating was discontinued and after the autoclave had returned to room temperature the excess pressure was discharged. The autoclave was opened and the reaction mixture was recovered therefrom. Gas chromatography analysis of the mixture showed a 50% conversion of the propylene with a 99.3% selectivity to isopropyl alcohol, the remainder of the product being diisopropyl ether.

When the above experiment was repeated with 407 grams of a 1.0% aqueous sulfuric acid solution and 6.45 grams of cobalt sulfate under operating conditions which included a pressure of 51 atmospheres, a temperature of 202° C., and a residence time of 2 hours, the gas chromatography analysis showed a 31% conversion of the propylene with an approximate 100% selectivity to isopropyl alcohol.

We claim as our invention:

1. A process for the direct hydration of an olefinic compound which comprises treating said olefinic compound with a dilute aqueous sulfuric acid solution in the presence of cobalt sulfate at a temperature of from about 100° to 300° C. and a pressure of from about 1 to about 250 atmospheres, the concentration of sulfuric acid in said solution being from about 0.05 to about 40% by weight, and recovering the resultant alcohol.

2. The process as set forth in claim 1 in which said olefinic compound is ethylene and said hydrated compound is ethyl alcohol.

3. The process as set forth in claim 1 in which said olefinic compound is propylene and said hydrated compound is isopropyl alcohol.

4. The process as set forth in claim 1 in which said olefinic compound is butylene and said hydrated compound is sec-butyl alcohol.

* * * * *